US005766201A

United States Patent [19]
Ravenscroft et al.

[11] Patent Number: 5,766,201
[45] Date of Patent: Jun. 16, 1998

[54] EXPANDABLE CATHETER

[75] Inventors: Adrian C. Ravenscroft, Boston; David L. Sandock, Littleton, both of Mass.

[73] Assignee: Boston Scientific Corporation, Natick, Mass.

[21] Appl. No.: 484,429

[22] Filed: Jun. 7, 1995

[51] Int. Cl.$^6$ ............................................ A61M 29/00
[52] U.S. Cl. ..................................... 606/194; 606/108
[58] Field of Search ............................... 606/194, 192, 606/193, 196, 198; 604/96, 97, 98, 104, 102, 191

[56] References Cited

U.S. PATENT DOCUMENTS

| | | |
|---|---|---|
| 1,690,995 | 11/1928 | Pratt. |
| 3,045,677 | 7/1962 | Wallace. |
| 3,173,418 | 3/1965 | Baran. |
| 3,736,939 | 6/1973 | Taylor. |
| 4,261,339 | 4/1981 | Hanson et al.. |
| 4,327,736 | 5/1982 | Inoue. |
| 4,338,942 | 7/1982 | Fogarty. |
| 4,346,698 | 8/1982 | Hanson et al.. |
| 4,423,725 | 1/1984 | Baran et al.. |
| 4,490,421 | 12/1984 | Levy. |
| 4,564,014 | 1/1986 | Fogarty et al.. |
| 4,608,984 | 9/1986 | Fogarty. |
| 4,637,396 | 1/1987 | Cook. |
| 4,685,447 | 8/1987 | Iversen et al.. |
| 4,702,252 | 10/1987 | Brooks et al.. |
| 4,709,698 | 12/1987 | Johnston et al.. |
| 4,733,665 | 3/1988 | Palmaz. |
| 4,740,207 | 4/1988 | Kreamer. |
| 4,819,751 | 4/1989 | Shimada et al.. |
| 4,846,174 | 7/1989 | Willard et al.. |
| 4,884,573 | 12/1989 | Wijay et al.. |
| 4,921,483 | 5/1990 | Wijay et al.. |
| 5,007,926 | 4/1991 | Derbyshire. |
| 5,030,227 | 7/1991 | Rosenbluth et al.. |
| 5,066,298 | 11/1991 | Hess ................................. 606/194 |
| 5,078,726 | 1/1992 | Kreamer. |
| 5,090,958 | 2/1992 | Sahota. |
| 5,108,416 | 4/1992 | Ryan et al.. |
| 5,112,304 | 5/1992 | Barlow et al.. |
| 5,116,318 | 5/1992 | Hillstead. |
| 5,137,512 | 8/1992 | Burns et al.. |
| 5,147,302 | 9/1992 | Euteneuer et al.. |
| 5,158,548 | 10/1992 | Lau et al.. |
| 5,171,221 | 12/1992 | Samson. |
| 5,171,297 | 12/1992 | Barlow et al.. |
| 5,181,911 | 1/1993 | Shturman. |
| 5,195,969 | 3/1993 | Wang et al.. |
| 5,195,972 | 3/1993 | Inoue. |
| 5,201,706 | 4/1993 | Noguchi et al.. |
| 5,201,757 | 4/1993 | Heyn et al.. |
| 5,207,700 | 5/1993 | Euteneuer. |
| 5,209,728 | 5/1993 | Kraus et al.. |
| 5,211,654 | 5/1993 | Kaltenbach. |
| 5,226,880 | 7/1993 | Martin. |
| 5,242,399 | 9/1993 | Lau et al.. |
| 5,254,091 | 10/1993 | Aliahmad et al.. |
| 5,290,306 | 3/1994 | Trotta et al.. |
| 5,295,962 | 3/1994 | Crocker et al.. |
| 5,304,135 | 4/1994 | Shonk. |
| 5,312,430 | 5/1994 | Rosenbluth et al.. |
| 5,330,429 | 7/1994 | Noguchi et al.. |
| 5,338,299 | 8/1994 | Barlow. |

(List continued on next page.)

*Primary Examiner*—Michael Buiz
*Assistant Examiner*—Kevin Truong
*Attorney, Agent, or Firm*—Fish & Richardson P.C.

[57] ABSTRACT

Treating a site within the body by, e.g., placing an endoprosthesis into the body, with a catheter having a proximal portion remaining outside the body and a shaft for positioning inside the body. The shaft includes in a distal portion a selectively expandable member which can be expanded from a small cross-sectional profile for receiving said endoprosthesis about said expandable member in a compact configuration and a large, expanded cross-sectional profile for expanding said prosthesis during placement into the body, and an elastic strip wrapped in helical fashion about said expandable member such that the strip is stretched when said expandable member is expanded to said large cross-sectional profile.

22 Claims, 5 Drawing Sheets

U.S. PATENT DOCUMENTS

| | | |
|---|---|---|
| 5,342,305 | 8/1994 | Shonk . |
| 5,344,402 | 9/1994 | Crocker . |
| 5,352,199 | 10/1994 | Tower . |
| 5,352,236 | 10/1994 | Jung et al. . |
| 5,358,486 | 10/1994 | Saab . |
| 5,366,472 | 11/1994 | Hillstead ................................ 606/194 |
| 5,370,618 | 12/1994 | Leonhardt . |
| 5,391,172 | 2/1995 | Williams et al. . |
| 5,409,495 | 4/1995 | Osborn . |
| 5,458,605 | 10/1995 | Klemm . |

EXPANDABLE CATHETER

This invention relates to a catheter including an expandable member, such as a balloon, for dilatation or delivery of an endoprosthesis.

BACKGROUND

Catheters with an expandable member, such as a balloon, are used to treat body lumens that have been occluded or weakened by disease. In angioplasty, for example, a catheter is threaded through the vasculature to locate the balloon at the site of an occlusion where the balloon is inflated to dilate the lumen. To maintain the lumen in a dilated condition, a tubular endovascular prosthesis may be provided at the site. The prosthesis is placed over the balloon such that, when the balloon is inflated, the prosthesis is expanded into contact with the wall to hold the lumen open. To treat aneurysms, a graft may be provided over the balloon. The ends of the graft are attached to healthy portions of the lumen on either side of the aneurysm so that the body of the graft bridges the weakened area.

SUMMARY OF THE INVENTION

In an aspect, the invention features treating a stricture site inside the body of a patient. The site is treated by providing a system including a catheter having a proximal portion remaining outside the body and a flexible shaft that can be positioned inside the body. The shaft includes in a distal portion a selectively expandable member which can be expanded from a low profile for delivery to the site to an expanded profile for treating the site. The system also includes a strip wrapped in a helical fashion about the expandable member such that the strip is stretched when the expandable member is expanded to the expanded profile. The catheter is delivered to the site and the expandable member expanded to treat the site.

In another aspect, the invention features a system for placing an endoprosthesis at an implantation site in the body of a patient. The system includes a catheter having a proximal portion remaining outside the body and a flexible shaft that can be positioned inside the body. The shaft includes in a distal portion a selectively expandable member which can be expanded from a low profile for receiving the endoprosthesis in a compact configuration for delivery to the site and an expanded profile for implanting the prosthesis at the site. The system also includes a strip wrapped in a helical fashion about the expandable member such that the strip is stretched when the expandable member is expanded to the expanded profile.

In another aspect, the invention features a system for placing an endoprosthesis at an implantation site in the body of a patient. The system includes a catheter having a proximal portion remaining outside the body and a shaft for positioning inside the body. The shaft includes in a distal portion a selectively expandable inflatable balloon which can be expanded from a small cross-sectional profile for receiving the endoprosthesis in a compact configuration for delivery to the site and an expanded cross-sectional profile for implanting the prosthesis at the site. The system also includes an elastic strip attached to the catheter at opposite ends of the balloon and wrapped in a series of overlapping turns about the balloon such that the strip is elastically stretched when the balloon is expanded and elastically recovers when the expandable member is collapsed after implantation of the prosthesis.

Embodiments may also include one or more of the following. The strip provides greater resistance to expansion in one part of the expandable member than another part of the expandable member such that the parts expand sequentially as expansion force is increased. The central portion of the expandable member expands prior to end portions proximal and distal thereof. The distal end portion expands prior to portions proximal thereof. The strip is wrapped in a manner that the wrap angle of the helical turns varies at locations corresponding to different parts of the expandable member. The wrap angle is greater at a location corresponding to a first part of the expandable member than at a location corresponds to a second part of the expandable member to permit inflation of the first part prior the second part as expansion force is increased. The wrap angle is greater in a central portion than in portions proximal and distal thereof. The wrap angle between helical turns is greater in a distal portion than in proximal portions.

Embodiments may also include one or more of the following. The strip is wrapped in a manner that the tension of the strip varies at locations corresponding to different parts of the expandable member. The geometry of the strip varies at locations corresponding to different parts of the expandable member. The strip is wider at a location corresponding to one portion then at a location corresponding to another portion. The strip is thicker at a location corresponding to one portion then at a location corresponding to another portion. The strip is attached to the catheter shaft at a location proximal and distal of the expandable member. The strip has a relatively low friction surface facing the prosthesis and a relatively high friction surface facing the balloon. The expandable member is a fluid-inflatable balloon. The balloon is formed of a nondistendible polymer. The prosthesis is formed of polymeric material. The prosthesis includes polymeric material with metal stents at its ends. The catheter is delivered and withdrawn through an endoscope. The system further includes members extending over the ends of the prosthesis when the ends are in a compact profile condition and the members are slidable from the ends when the ends are expanded to the expandable profile.

Embodiments may include one or more of the following advantages. The helically wrapped strip can be used to vary the sequence of inflation of different portions of an expandable member, such as a balloon and an overlying prothesis, by varying the nature of the wrap about the corresponding portions to effect differing resistance to expansion force. In particular cases, the strip is wrapped in a manner that a central portion inflates prior to distal and proximal portions or in a manner that a distal portion inflates prior to more proximal portions. These inflation sequences may have particular advantages when using the system to expand a prosthesis including a highly malleable material such as PTFE or other polymer. By expansion of the central or distal portion first, the malleable graft will not be pushed off the end of the catheter, as might be the case if the proximal portion is inflated first. Nor will the prosthesis be axially compressed, as might occur if both the proximal and distal portions are inflated prior to the central portion.

In addition, the wrap may have a slippery surface compared to conventional balloon materials, such as PET, so that a polymer prosthesis is readily released from the balloon after it is expanded. (The stickiness between PET and PTFE is believed to be caused by surface tension interaction between these two smooth-surface materials or due to localized vacuum effects caused by the porous nature of the PTFE.) Further, in cases where the wrap exhibits elasticity, it may reduce the profile of the balloon upon deflation by aiding balloon refolding.

Still further features, aspects, and advantages follow.

BRIEF DESCRIPTION OF THE DRAWINGS

FIG. 1 is an assembly drawing including a side view of a catheter including an expandable member with a helically wrapped strip and in cross-section, a prosthesis, which can be positioned over the wrapped expandable member, while

FIG. 2 is a side view of the distal portion of the system in FIG. 1 with the expandable member and prosthesis in an initial stage of expansion, while FIG. 2A is a cross-sectional view along the line 2A2A in FIG. 2;

FIG. 3 is a side view, in partial cross-section, of the distal portion of the catheter in FIG. 2 with the expandable portion and prosthesis fully expanded, while

FIG. 4 is a side view of the catheter in FIG. 3 after the expandable member has been collapsed, while FIG. 4A is a cross-sectional view along line 4A4A in FIG. 4;

FIG. 5 is a view of an elastic strip prior to wrapping, while

FIG. 11 is a side view of another catheter including an expandable member and a helically wrapped strip, while

STRUCTURE AND OPERATION

Referring to FIGS. 1–4A, a system 10 for placing a prosthesis 26 into the body includes a catheter 12 that has a flexible shaft 14 with an expandable portion 16 near its distal end. The expandable portion 16 includes an inflatable balloon 28 and a strip 18 that has been helically wrapped about the balloon. The prosthesis 26, which may be an expandable PTFE graft, is in a small diameter form and positioned over the helically wrapped strip for delivery into the body.

Figure 3:
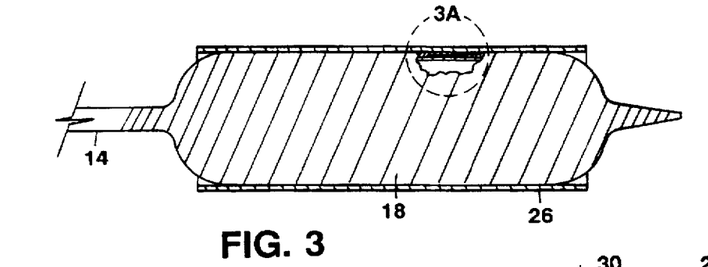
Figure 3A:
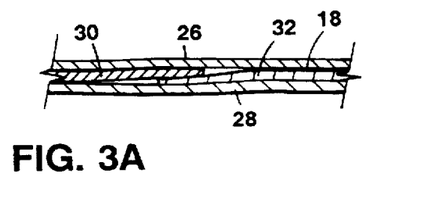
FIG. 3A is a greatly expanded cross-sectional view of the area in circle 3A in FIG. 3.

The strip is wrapped in a manner such that adjacent turns 30, 32, of the strip overlap (FIG. 3A). The wrap angle of the helical turns (and hence, the distance, or pitch length, between turns and the amount of overlap between adjacent turns) varies in different portions along the length of the balloon. In proximal portion 20 and distal portion 22 the wrap angle $\theta_1$, is greater than the wrap angle $\theta_2$ in the central portion 24. As discussed in more detail below, by decreasing the wrap angle of the helical pattern, greater material overlap occurs and, consequently greater resistance to radial inflation force, which permits expansion of the central portion before expansion of the distal and proximal portions as inflation pressure is increased.

Figure 1:
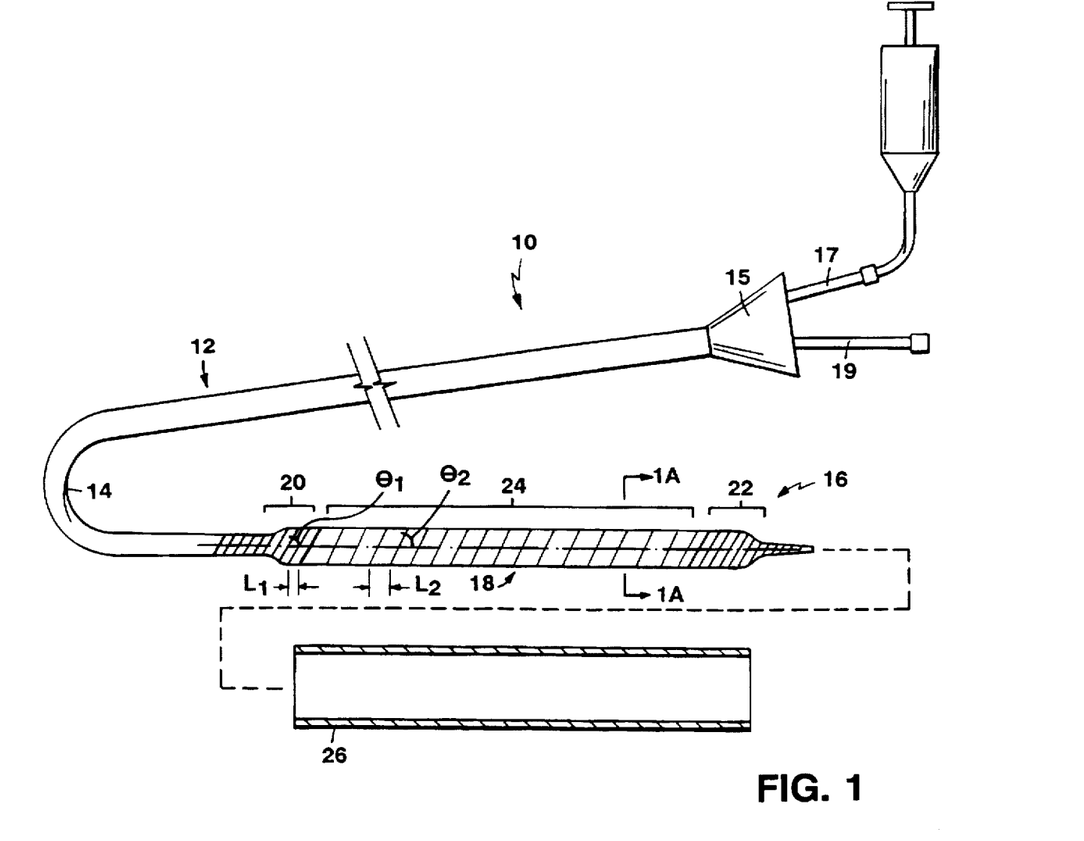
Figure 1A:
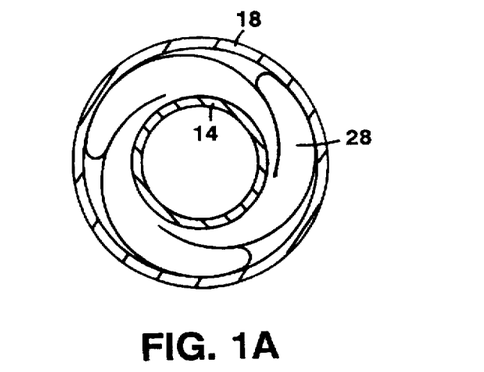
FIG. 1A is a cross sectional view along the line 1A1A of FIG. 1.

Referring particularly to FIGS. 1 and 1A, prior to delivery into the body, the balloon 28 is in a low profile, deflated condition. Typically, the balloon is wrapped around the catheter body in a series of overlapping wings or folds (FIG. 1A). The strip is formed of an elastic material, is helically wrapped to closely conform to and lightly compress the folded balloon. The prosthesis 26, in a small cross-sectional profile condition, can be slipped over the helically wrapped strip. To retain the prosthesis during delivery into the body, the balloon may be partially inflated to securely grip the prosthesis or the strip may have a roughened, high friction outer surface. Alternatively, a retractable sheath can be placed over the prosthesis. The catheter 12 also includes a proximal portion remaining outside the body that includes a hub 15 with a port 17 for introduction of inflation fluid to an internal lumen communicating with the interior of the balloon and a port 19 communicating with an interior lumen in a manner to permit delivery of the device over a guide wire.

Figures 2, 2A:
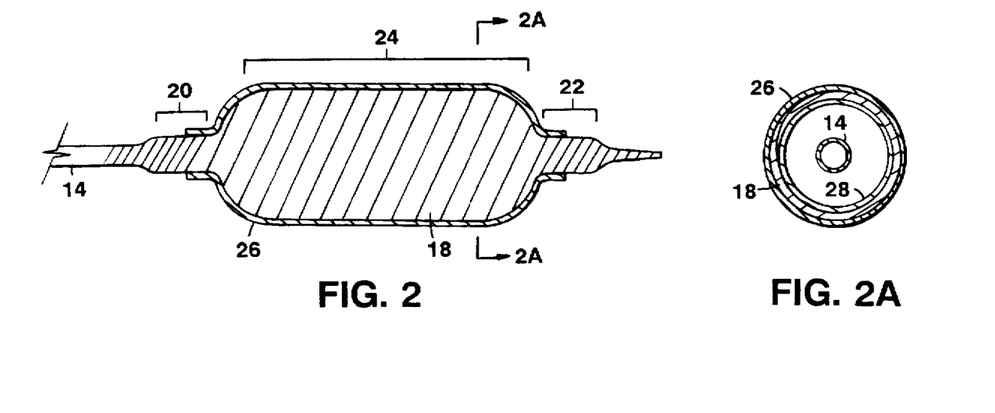

Referring particularly to FIGS. 2 and 2A, after the catheter is threaded into the body to locate the prosthesis at a desired implantation site (not shown), the balloon is inflated to an initial inflation pressure which is sufficient to overcome the resistance of the helically wrapped strip in the central portion 24. The strip stretches elastically as the balloon unfolds and expands, causing the corresponding central portion of the prosthesis 26 to be expanded into contact with the wall of a body lumen at an implantation site. However, the proximal and distal portions 20, 22, where the strip is wrapped to provide greater radial resistance, remain substantially unexpanded. The proximal and distal portions include the taper regions of the balloon, which are not beneath the prosthesis, to keep the taper portions from expanding against the body lumen and to give the expanded central portion a more uniform cylindrical shape.

Referring to FIG. 3, upon inflation to higher pressures, the resistance to expansion at the proximal 20 and distal portions 22 is overcome, allowing those portions to expand and causing the corresponding portions of the prosthesis to be expanded into contact with the body lumen wall.

Figures 4, 4A:
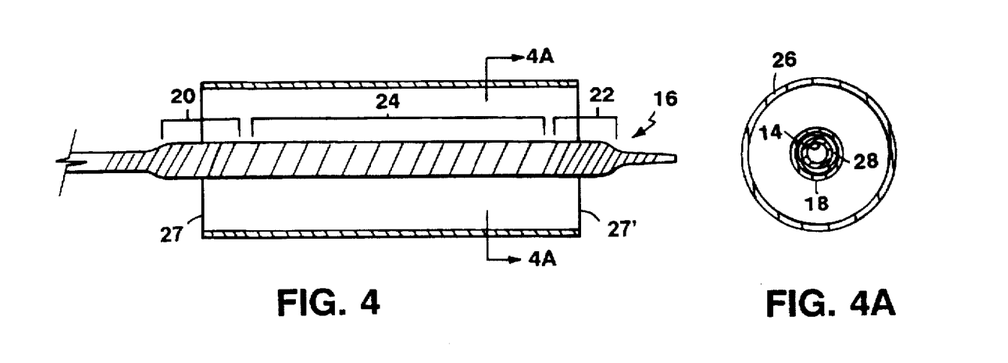

Referring to FIGS. 4 and 4A, after the prosthesis has been fully expanded, the pressure in the balloon is released. The helically wrapped strip elastically recovers and the catheter is removed from the body while leaving the prosthesis at the implantation site.

The elastic strip may also help refold the balloon about the catheter. During inflation the wrap is subject to non-uniform strain as the balloon rotates as it unfolds. The effect of this non-uniform strain is remembered by the wrap. Upon deflation, the helically wrapped strip recovers from these nonuniform forces by twisting slightly around the shaft. In addition, the helical turns may rotate somewhat relative to each other during inflation in response to the local underlying forces and then rotate back during deflation, which also has the effect of aiding balloon refolding.

The helically wrapped strip delivery system may provide particular advantages in delivering polymeric grafts, such as those including PTFE. Arranging the system to expand the central portion prior to the end portions avoids compression of a prothesis made of relatively malleable polymer materials that may occur if the end portions were expanded prior to central portion. These advantages may be of particular importance when using a graft in which the central portion is formed of polymer, e.g., PTFE, that is not supported by a metal stent. For example, the graft may be a continuous tube of polymer of a tube including metal anchoring stents at the proximal and distal ends. In addition, the strip may be formed of a material that is less tacky and does not adhere to the prosthesis as much as a glassy, crystalline balloon polymers such as PET, which permits the prosthesis to be more easily released from the catheter after expansion.

Manufacture

Figure 5:
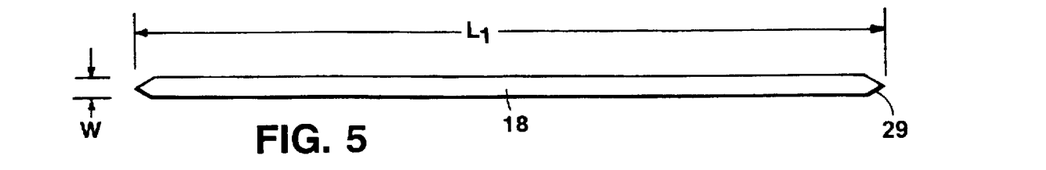
Figure 5A:
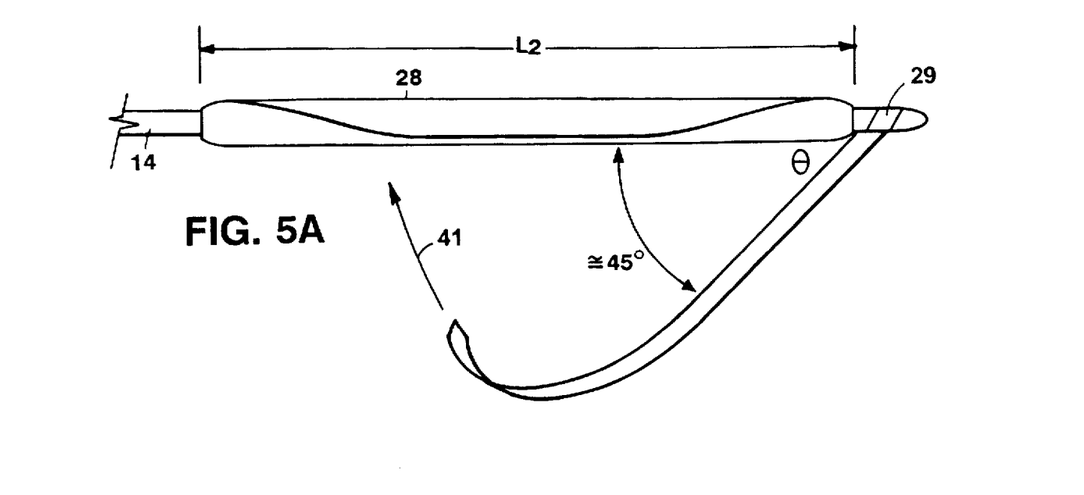
FIG. 5A is a schematic illustrating helical wrapping of the strip about an expandable member.

Referring to FIGS. 5–5B, strip 18 is helically wrapped by bonding an end 29 to the catheter shaft at a location that is adjacent and distal of the balloon (FIG. 5A). The ends of the strip are trimmed to a point prior to wrapping to avoid excess at the leading and trailing edges. The strip is then placed in light tension as it is rotated about the catheter (arrow 41) in a manner that each turn of the helix overlaps the previous turn, which keeps the previous turn from unwrapping. After the entire length of balloon has been wrapped, the opposite end of the strip is bonded to the catheter at a location that is proximal to the balloon.

The strip may be made of an elastic material with an elongation of about 550–800 percent or more. Examples include urethanes, silastics and latex. In a particular embodiment, the strip is made of an elastic urethane (available as HT-7 from Apex Corp. CA) and is cut to a length of about 8–10 cm (depending on balloon length), a width of about 12 mm, and a thickness of about 0.002". The catheter is a nylon angioplasty catheter including a wing-folded PET balloon with a length of about 2–10 cm and an inflation diameter of about 6–10 mm which is available as the Ultrathin ST-UT Balloon Catheter from Boston Scientific Corporation, Natick, Mass. This catheter includes a balloon with relatively short taper regions, 5–8 mm (depending on inflation diameter), which reduces the length of balloon beyond the prosthesis that must be wrapped with the strip. In the wrapping step, the strip is typically stretched less than 200% to avoid cold flow effects during storage, particularly when latex is used. Greater resistance to expansion force can be effected by increasing the number of turns over a portion of the balloon, which increases the overlap of adjacent turns, and can be achieved by increasing the wrap angle, θ. In the particular case, the wrap angle may be about 50°–60° over a length of about 2–3 cm in proximal and distal portions and the wrap angle may be about 4–25 cm (depending upon balloon length) in the central portion. At a wrap angle of about 45°, the balloon typically inflates at a minimum pressure of about 1.5 to 3 atm. At a wrap angle of about 50° to 60° the balloon inflates at about 4 to 5 atm. The prosthesis is formed of a polymeric material, such as expanded, and expandable, PTFE. suitable prostheses of this type are taught in Colone, U.S. Ser. No. 08/239,239 filed May 6, 1994, and U.S. Ser. No. 08/265,794 filed Jun. 27, 1994 and a PCT application entitled "Radially Expandable Polytetrafluoroethylene and Expandable Endovascular Stents Formed Therewith" filed on Jun. 7, 1995, the entire contents of which is incorporated herein by reference. The PTFE prosthesis may include metal stent anchors which may be formed of thermal effect shape memory nitinol as taught in Simon et al. U.S. Pat. No. 5,354,308 the contents of which is incorporated herein by reference. In embodiments, the prosthesis may include a metal stent along its entire length. The stent may also be balloon expandable materials such as stainless steel or tantalum. The stent may extend the full length of PTFE graft. The stent may be attached to the polymer, e.g., with suture or positioned within the polymer without attachment.

Other Embodiments

An elastic strip may be stretched beyond its elastic limit such that it only partially recovers. This operational mode may be used with larger balloons, e.g., 12–14 mm inflated diameter. The strip may also be formed of a non-elastic but malleable material, e.g., Teflon. In such cases, the strip can control expansion sequence by varying wrap parameters or strip construction along its length and plastically stretching, but the strip does not recover elastically upon deflation.

The strip may be tacky on one side, for example, the side in contact with the balloon, and slippery on the other side, which is exposed to the interior of the prosthesis to aid release of the prosthesis after expansion. This effect may be achieved by roughening the inner surface of the strip, e.g., forming the strip by dipping using a mandrel with a roughened surface. The strip may also be provided with a low-friction coating, such as Teflon or a hydrogel. A low friction material may be provided by coextrusion of multiple layers on the strip.

The wrap may also be imbibed with a drug, such as heparin, which is squeezed out of the polymer when wrap is stretched during expansion. The drug may be imbibed during manufacture of the strip. Alternatively, the drug may be absorbed in the strip by dipping into a drug solution just prior to use. For example, the balloon could be inflated, dipped into a drug solution, deflated while in the solution to draw drug into polymer and then removed from the drug solution.

Figure 6:
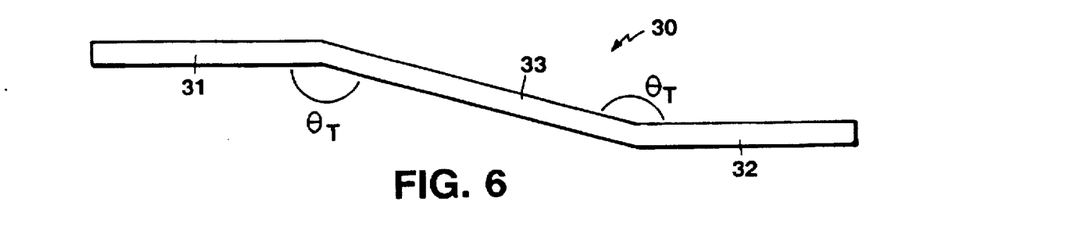
FIG. 6 is a view of another strip which can be helically wrapped about an expandable member.

Refer to FIG. 6, the wrap angle can be varied by constructing the strip to include preselected angular transitions. A strip 30, for example, includes portions 31, 32, to be wrapped around the ends of the balloon, that transition at angles with respect to a portion 33 that is wrapped about the central portion of the balloon. The transition angles avoid additional compression at the helical turn where the wrap angle changes.

Figure 7:
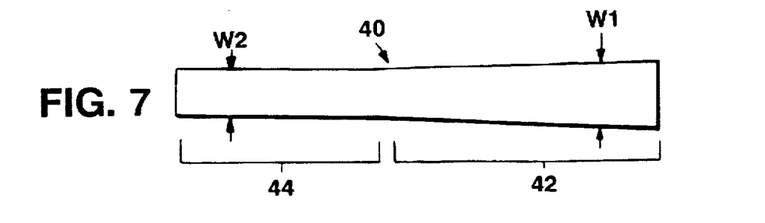
FIG. 7 is another strip which can be helically wrapped about an expandable member.
Figure 8:
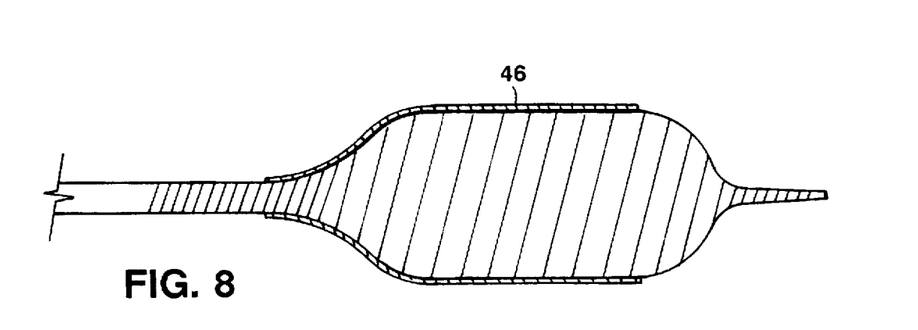
FIG. 8 is a side view of a catheter including the strip in FIG. 7 helically wrapped about expandable member and in an initial stage of expansion.
Figure 9:
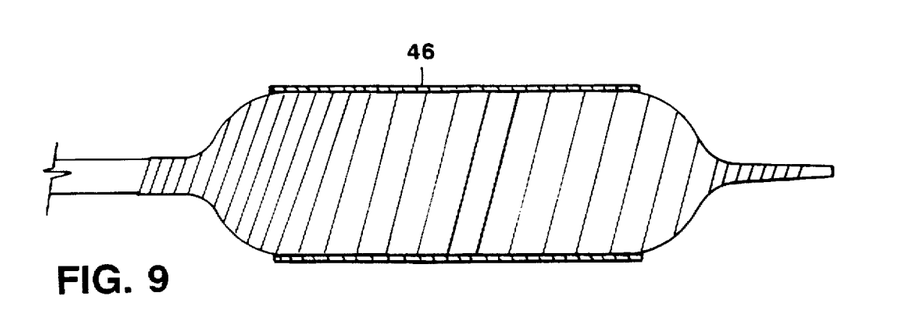
FIG. 9 is a view similar to FIG. 9 with the expandable member fully expanded.

Referring to FIGS. 7–9, a strip 40 includes a relatively wide distal portion 42, width, W1, and a relatively narrow proximal portion 44 width, W2 (FIG. 7). As the width of the strip increases, the resistance decreases for a strip wrapped of constant angle and tension. At an initial inflation pressure, the distal portion of the balloon, corresponding to the location of the distal portion of the strip 42, expands which causes expansion of the corresponding distal portion of a prosthesis 46 (FIG. 8). Upon inflation to higher pressures, the proximal portion expands, corresponding to the proximal portion 44 of the strip, permitting the more proximal portions of the prosthesis 46 to be expanded (FIG. 9). By arranging the system to expand the distal portion prior to more proximal portions, the likelihood that the prothesis will be pushed or extruded off the end of the catheter is minimized, particularly in the case of polymer grafts.

Resistance to expansion force can be varied by varying other parameters of the strip. For example, the tension of the strip can be varied during wrapping to the effect that greater tension causes an increase in resistance to expansion force. The thickness of the strip may be varied along its length. The composition of the strip may also be varied along its length. In embodiments, the adjacent turns of the wrap need not overlap. For example, the adjacent turns may overlap only in the end portions corresponding to the balloon tapers to keep the wrap from slipping or bunching in the taper portions when the central portion is expanded. Multiple, concentrically wrapped strips can also be used. The strip may also be a composite or laminate of different materials to achieve effects as described above. Combinations of parameters can be used to vary the resistance. For example, the resistance can be varied by varying both the wrap angle and the wrap tension in the different portions. The strip may be wrapped for greater resistance at proximal and distal portions that correspond only to the taper portions of the balloon and do not extend beneath the prosthesis. The strip may also be wrapped to provide a constant resistance to expansion force along the entire length of the balloon to permit inflation of the entire balloon simultaneously.

Figure 10:
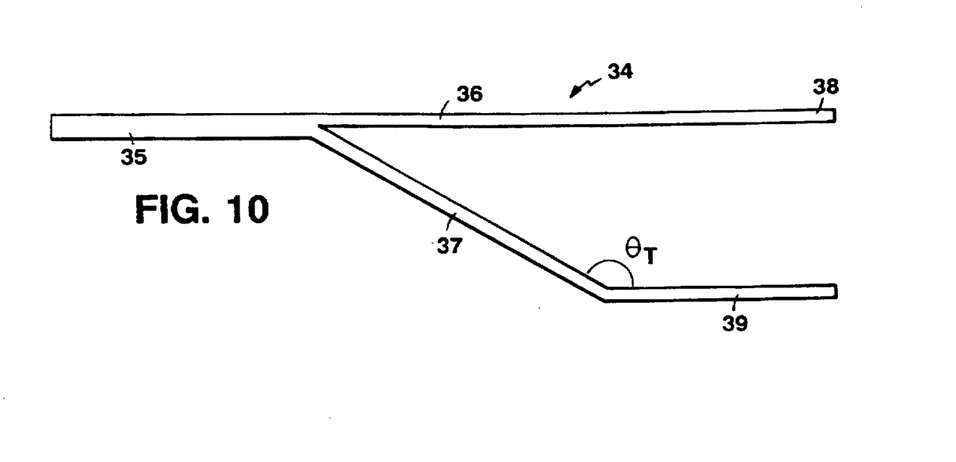
FIG. 10 is a view of another strip which can be helically wrapped about an expandable member.

Referring to FIG. 10, another strip 34 provides for double wrapping an expandable member. The strip includes and end portion 35, bifurcated central portions 36, 37 and second end portions 38, 39. The bifurcated central and second portions may be formed of the same or different materials, attached, e.g., by melt or adhesive bonding or coextrusion. The strip 34 is wrapped by first helically wrapping end portion 35, central portion 36 and end portion 38. The central portion 37 and end portion 39 are wrapped over portions 36, 38. The second wrapping may be provided with different wrap characteristics then the first wrapping.

The balloon catheter may be a conventional dilatation catheter with a dilatation balloon formed of PET, nylon, PE, or other suitable material. The prosthesis can be expanded simultaneously with dilatation of the a lumen or subsequently, after a separate dilatation procedure. In typical vascular applications, the balloon has a length between about 2–10 cm and an inflated diameter of about 5–8 mm. As discussed above, longer balloons can also be used. Larger diameter balloons may also be used, for example, balloons in the 10–14 mm diameter range. The balloon may not be wing folded but rather compressed uniformly about the catheter shaft.

Figure 11:
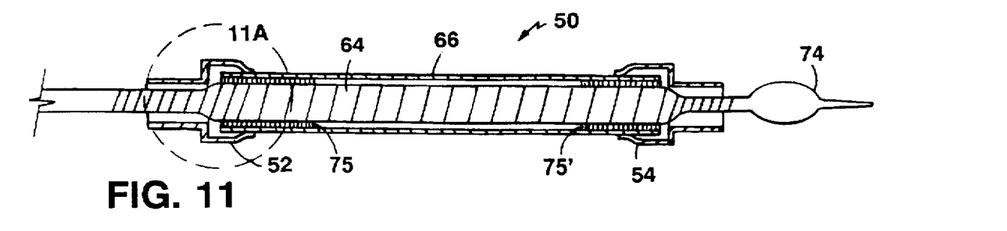
Figure 11A:
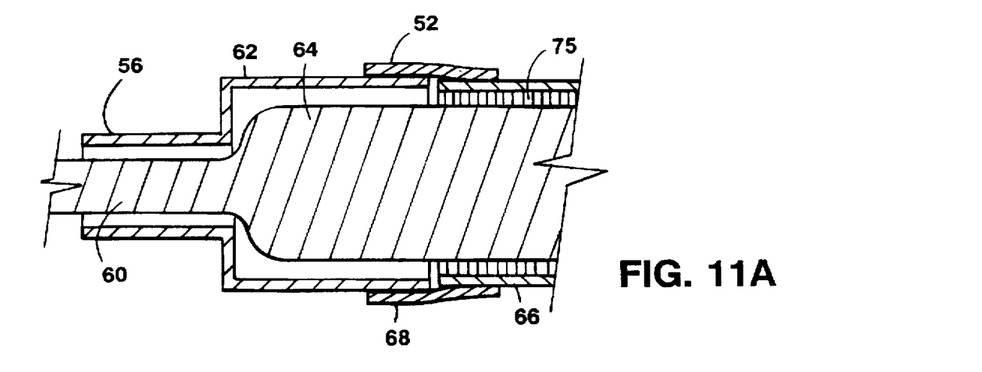
FIG. 11A is a greatly expanded view of the region in circle 11A in FIG. 11.
Figure 12:
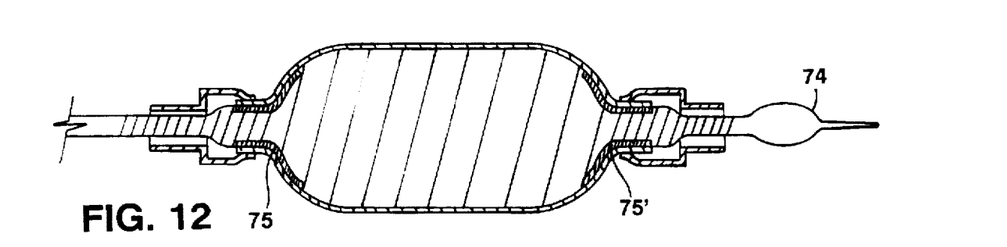
FIG. 12 is a side view similar to FIG. 11 with the expandable member in a state of initial expansion.
Figure 13:
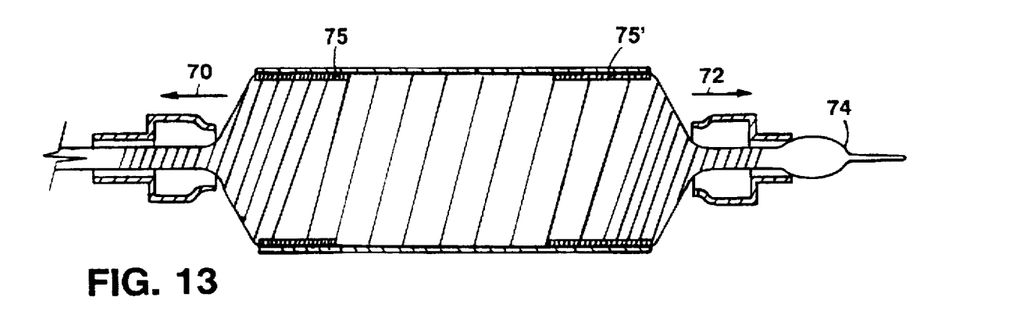
FIG. 13 is a side view similar to FIG. 12 with the expandable member fully expanded.

Referring to FIGS. 11–13, in embodiments, a catheter 50 may be provided with members 52, 54 (shown in cross-section) which hold the ends of the prosthesis stationary while the central portion is expanded but slide axially as the ends are expanded. Referring particularly to FIG. 11A, the members 52, 54 include a proximal portion 56 with a small inner diameter sized to fit closely over a catheter body 60 and a large end 62 with inner diameter sized to fit over the helically wrapped balloon 64 and prosthesis 66. The large diameter end includes an elastic extension 68 which grips the exterior of the prosthesis. The prosthesis 66 includes metal anchoring stents 75, 75' at its ends. The stents are made, e.g., of self-expanding thermal effect shape memory material that expands to larger diameter upon increase in temperature.

Referring particularly to FIG. 11, on initial inflation, the central portion of the balloon and prosthesis are expanded while the end portions remain substantially unexpanded. The members 52, 54 keep the stent from moving axially.

Referring to FIG. 11, upon inflation to higher pressure, the end portions expand, causing the members 52,54 to slide axially (arrows 70, 72) and permit full inflation. (The distal portion of the catheter includes a protrusion 74 to keep the member 54 from sliding off the end.)

In a particular embodiment, the members 52, 54 are formed of FEP (perfluoroethylene copolymer) with tubular extensions 52 made of silastic. The members can be constructed to keep the taper portions of the balloon from inflating before the central portion is inflated by providing sufficient resistance, in combination with the helical wrap, to shape the balloon inflation and avoid expansion of the taper regions. The members 52, 54 can also be used to keep the end portions from inflating in a system without a helical wrap. The members may also prevent self-expanding metal stents at the end of the prosthesis from expanding prior to balloon inflation. A slidable member is also discussed in Roberts, U.S. SER. No. 269,04, filed Jun. 30, 1994, the entire contents of which are incorporated herein by reference. In other embodiments, an elastic sleeve can be provided over the ends of the prosthesis. A sleeve is taught in Savin, U.S. Pat. No. 4,950,227, the entire contents of which is incorporated herein by reference.

In embodiments, the prosthesis may be made a polymer, such as PTFE, over a metal stent extending the full length of the prosthesis. In embodiments the prosthesis may be made entirely of a polymer such as PTFE, without any metal stent structure. The prosthesis may also be a metal stent without a polymer element. In embodiments, the metal stent may be a balloon expandable metal or a self-expanding material, such as a highly elastic nitinol material or thermal-effect shape memory material, that is implanted with balloon assist. The system may also provide particular advantages for delivering relatively long prosthesis, e.g. 15–20 cm in length, since the wrap can assist refolding of long balloons made of stiff, nondistendible polymers, such as PET.

The system can be used in and adapted for procedures such as dilatation or vascular stenting in, for example, the coronary or peripheral arteries. The system can also be constructed and arranged for placement of a graft for treating an aneurysm, e.g., in the aorta. The system may also be constructed and arranged for use in non-vascular body lumens and other body locations to treat occlusions or to treat other diseases. For example, the system can be used in endoscopic applications in which the catheter and balloon are introduced through and removed from the narrow working channel of an endoscope. Examples include treating esophageal and pyloric strictures, in which the system must pass through on endoscopic channel with an inner diameter of about 2.8 mm or treating colonic or anastomonic strictures in which the system must pass through a working channel of about 3.2 mm or treating biliary strictures, in which the system passes through a working channel about 2.8 to 4.2 mm in diameter. The system can also be used in dilation operations without delivering a prosthesis.

Further embodiments are in the following claims.

What is claimed is:

1. A system for placing an endoprosthesis having a proximal end and a distal end at an implantation site in a patient's body, comprising:

a catheter having a proximal portion remaining outside the patient's body and a flexible shaft that can be positioned inside the patient's body, said shaft including in a distal portion a selectively expandable member which can be expanded from a small diameter for receiving said endoprosthesis in a compact configuration for delivery to said site to a large diameter for implanting said endoprosthesis at said site, and a strip fixed to said catheter at opposite ends of said selectively expandable member and wrapped in a helical fashion about said expandable member such that said strip is stretched when said expandable member is expanded to said larger diameter.

2. The system of claim 1 wherein said expandable member comprises a first portion and a second portion, and wherein said strip provides greater resistance to expansion in said first portion of said expandable member than said second portion of said expandable member such that said second portion expands before said first portion as expansion force is increased.

3. The system of claim 1 wherein said expandable member comprises a proximal portion, a distal portion, and a central portion, wherein said central portion of said expandable member expands prior to said proximal and distal portions, as expansion force is increased.

4. The system of claim 3 wherein said strip is wrapped in a manner that the wrap angle is greater at a location corresponding to said central portion of said expandable member than at a location corresponding to said proximal and distal portions of said expandable member to permit inflation of said central portion prior to said proximal and distal portion as expansion force is increased.

5. The system of claim 2 wherein said strip is wrapped in a manner that the wrap angle of the helical turns varies at locations corresponding to different said portions of said expandable member.

6. The system of claim 2 or 3 wherein said strip is wrapped in a manner that the tension of said strip varies at locations corresponding to different portions of said expandable member.

7. The system of claim 2 wherein a geometry of said strip varies at locations corresponding to different parts of said expandable member.

8. The system of claim 7 wherein said strip is wider at a location corresponding to one portion of said strip than at a location corresponding to another portion of said strip.

9. The system of claim 7 wherein said strip is thicker at a location corresponding to one portion of said strip than at a location corresponding to another portion of said strip.

10. The system of claim 1 wherein said strip is elastically stretched when said expandable member is expanded and elastically recovers when said expandable member is collapsed after expansion.

11. The system of claim 1 wherein the strip has a relatively low friction surface facing said endoprosthesis and a relatively high friction surface facing said expandable member.

12. The system of claim 1 wherein said expandable member is a fluid-inflatable balloon.

13. The system of claim 1 wherein said expandable member is formed of a nondistendible polymer.

14. The system of claim 1 further comprising said endoprosthesis carried upon said catheter.

15. The system of claim 14 wherein said endoprosthesis is formed of polymeric material.

16. The system of claim 1 further including members, extending over said proximal and distal ends of said endoprosthesis when said ends are not expanded and said members being slidable from said ends when said ends are expanded.

17. A system for placing an endoprosthesis at an implantation site in patient's body, comprising:

a catheter having a proximal portion remaining outside the patient's body and a shaft for positioning inside the patient's body, said shaft including in a distal portion a selectively expandable inflatable balloon which can be expanded from a small diameter for receiving said endoprosthesis in a compact configuration for delivery to said site and a large diameter for implanting said endoprosthesis at said site, said balloon having proximal portion, distal portion, and central portion and an elastic strip attached to said catheter at opposite ends of said balloon and wrapped in a series of overlapping turns, each turn defining a wrap angle, said wrapping being about said balloon such that said strip is elastically stretched when said balloon is expanded and elastically recovers when said balloon is collapsed after implantation of said endoprosthesis.

18. The system of claim 17 wherein the wrap angle is greater at a location corresponding to said central portion of said balloon than at a location corresponds to portions of said balloon proximal and distal thereof to permit inflation of said central portion prior said proximal and distal portions as inflation force is increased.

19. The system of claim 17 further comprising an endoprosthesis carried upon said catheter.

20. A method for treating a stricture site inside a body of a patient, comprising:

providing a system including a catheter having a proximal portion remaining outside the body and a flexible shaft that can be positioned inside the body, said shaft including in a distal portion a selectively expandable member which can be expanded from a low profile for delivery to said site and an expanded profile for treating said site, and a strip wrapped in a helical fashion about said expandable member such that said strip is stretched when said expandable member is expanded to said expanded profile, delivering said catheter to said site, and expanding said expandable member to treat said site.

21. The method of claim 20 wherein said strip is elastically stretched when said expandable member is expanded and elastically recovers when said expandable member is collapsed after expansion.

22. The method of claim 20 comprising delivery and withdrawal of said catheter through an endoscope.

* * * * *